(12) United States Patent
Correale

(10) Patent No.: US 8,648,293 B2
(45) Date of Patent: Feb. 11, 2014

(54) CALIBRATION OF MASS SPECTROMETRY SYSTEMS

(71) Applicant: Agilent Technologies, Inc., Loveland, CO (US)

(72) Inventor: Raffaele Correale, Turin (IT)

(73) Assignee: Agilent Technologies, Inc., Loveland, CO (US)

( * ) Notice: Subject to any disclaimer, the term of this patent is extended or adjusted under 35 U.S.C. 154(b) by 0 days.

(21) Appl. No.: 13/661,486

(22) Filed: Oct. 26, 2012

(65) Prior Publication Data

US 2013/0043380 A1     Feb. 21, 2013

Related U.S. Application Data

(63) Continuation-in-part of application No. 12/831,945, filed on Jul. 7, 2010.

(30) Foreign Application Priority Data

Jul. 8, 2009 (IT) .............. TO2009A0513
May 13, 2010 (IT) .............. TO2010A0399

(51) Int. Cl.
*H01J 49/04* (2006.01)
*H01J 49/26* (2006.01)

(52) U.S. Cl.
USPC ................... 250/252.1; 250/288

(58) Field of Classification Search
USPC .......... 250/281–283, 288, 423 R, 424; 95/43, 95/45, 291
See application file for complete search history.

(56) References Cited

U.S. PATENT DOCUMENTS

| | | | | |
|---|---|---|---|---|
| 3,455,092 A | * | 7/1969 | Llewellyn | ............................ 96/5 |
| 3,455,902 A | | 7/1969 | Llewellyn | |
| 3,712,111 A | * | 1/1973 | Llewellyn | .................... 73/23.37 |
| 3,751,880 A | * | 8/1973 | Holm | .................................. 96/5 |
| 4,008,388 A | * | 2/1977 | McLafferty et al. | ............ 702/27 |

(Continued)

FOREIGN PATENT DOCUMENTS

| | | |
|---|---|---|
| EP | 1764823 A2 | 3/2007 |
| JP | 2001155677 A1 | 6/2008 |

(Continued)

OTHER PUBLICATIONS

Maden et al., "Sheet Materials for Use as Membranes in Membrane Introduction Mass Spectrometry," Analytical Chemistry, American Chemical Society, May 15, 1996, vol. 68, No. 10, pp. 1805-1811, US.

(Continued)

*Primary Examiner* — Bernard E Souw

(57) ABSTRACT

A method for operating a mass spectrometer (MS) includes establishing a pressure differential across a membrane wherein an upstream pressure in a calibrant gas inlet line on an upstream side of the membrane is greater than a downstream pressure in an ion source on a downstream side of the membrane; flowing a calibrant gas from the calibrant gas inlet line, through a nano-scale orifice of the membrane, and into the ion source; and maintaining the upstream pressure at a constant value. The calibrant may be flowed at a low flow rate. An MS system includes a membrane interposed between a calibrant gas introduction system and a mass spectrometer. The membrane may include an orifice of nano-scale diameter.

20 Claims, 9 Drawing Sheets

(56) References Cited

U.S. PATENT DOCUMENTS

| | | | |
|---|---|---|---|
| 4,051,372 A * | 9/1977 | Aine | 250/343 |
| 4,311,669 A * | 1/1982 | Spangler | 422/98 |
| 4,551,624 A * | 11/1985 | Spangler et al. | 250/287 |
| 4,712,008 A | 12/1987 | Vora et al. | |
| 4,804,839 A * | 2/1989 | Broadbent et al. | 250/288 |
| 6,006,584 A * | 12/1999 | Itoi | 73/23.37 |
| 6,039,792 A * | 3/2000 | Calamur et al. | 95/45 |
| 6,822,226 B2 | 11/2004 | Ross et al. | |
| 7,037,425 B2 | 5/2006 | Lee et al. | |
| 7,155,076 B2 | 12/2006 | Letant et al. | |
| 7,217,919 B2 | 5/2007 | Boyle et al. | |
| 7,361,888 B1 | 4/2008 | Boyle et al. | |
| 7,528,366 B1 | 5/2009 | Boyle et al. | |
| 7,582,867 B2 | 9/2009 | Wells et al. | |
| 7,608,818 B2 * | 10/2009 | Miller et al. | 250/288 |
| 7,690,241 B2 * | 4/2010 | Muntz et al. | 73/31.07 |
| 7,803,274 B2 * | 9/2010 | Taylor et al. | 210/321.81 |
| 8,237,116 B2 * | 8/2012 | Correale | 250/288 |
| 8,337,588 B2 * | 12/2012 | Shqau et al. | 95/51 |
| 2001/0029841 A1 * | 10/2001 | Li et al. | 95/45 |
| 2002/0134933 A1 | 9/2002 | Jenkins et al. | |
| 2003/0001085 A1 * | 1/2003 | Bateman et al. | 250/281 |
| 2003/0038245 A1 * | 2/2003 | Hartley | 250/423 R |
| 2003/0071223 A1 * | 4/2003 | Hartley et al. | 250/423 F |
| 2003/0111948 A1 * | 6/2003 | Retsky | 313/364 |
| 2006/0091308 A1 | 5/2006 | Boyle et al. | |
| 2007/0131860 A1 * | 6/2007 | Freeouf | 250/292 |
| 2008/0168752 A1 | 7/2008 | Smith et al. | |
| 2008/0178658 A1 | 7/2008 | Muntz et al. | |
| 2009/0272684 A1 | 11/2009 | Taylor et al. | |
| 2009/0294657 A1 | 12/2009 | Rafferty | |
| 2010/0223979 A1 | 9/2010 | Ploehn et al. | |
| 2011/0006202 A1 * | 1/2011 | Correale | 250/288 |
| 2011/0247492 A1 * | 10/2011 | Shqau et al. | 95/51 |
| 2012/0208004 A1 * | 8/2012 | Wolcott et al. | 428/315.7 |
| 2013/0043380 A1 | 2/2013 | Correale | |

FOREIGN PATENT DOCUMENTS

| | | |
|---|---|---|
| WO | 0135441 A1 | 5/2001 |
| WO | 03049840 A1 | 6/2003 |
| WO | 2008074984 A1 | 6/2008 |

OTHER PUBLICATIONS

European Search Report dated Aug. 18, 2010.
European Interview Summary dated Jun. 1, 2012.
Response to EP Office Action dated Jul. 9, 2012.

* cited by examiner

CALIBRATION OF MASS SPECTROMETRY SYSTEMS

RELATED APPLICATIONS

This application is a continuation-in-part of U.S. patent application Ser. No. 12/831,945, filed Jul. 7, 2010, titled "GAS SAMPLING DEVICE AND GAS ANALYZER EMPLOYING THE SAME", which claims the benefit of Italian Patent Application Serial No. TO2009A000513, filed Jul. 8, 2009, and further claims the benefit of Italian Patent Application Serial No. TO2010A000399, filed May 13, 2010; the contents of all of which are incorporated by reference herein in their entireties. This application is related to U.S. patent application Ser. No. 12/831,921, filed Jul. 7, 2010, titled "GC-MS ANALYSIS APPARATUS", now issued as U.S. Pat. No. 8,237,116, the content of which is incorporated by reference herein in its entirety.

TECHNICAL FIELD

The present invention relates generally to calibration of mass spectrometry (MS) systems, including gas chromatography-mass spectrometry (GC-MS) systems, and in particular relates to introducing a calibrant gas into a mass spectrometer under constant-pressure, very low flow conditions.

BACKGROUND

Mass spectrometry is used for analyzing substances that can be brought to the gas phase under high-vacuum conditions, i.e. under pressures generally ranging between about $10^{-2}$ and $10^{-6}$ Pa or lower. Although the present subject matter is not limited to this field of use, reference in the following description will therefore be made primarily to this analysis method.

Mass spectrometry is a known analytical technique applied to both the identification and analysis of known substances. The principle on which it is based is the possibility of separating a mixture of ions depending on their mass/charge (m/z) ratio generally by applying electric or magnetic fields, either static or oscillating.

There are different ways to volatize and ionize a sample, and there are many different kinds of ion sources, such as EI (electron impact) source, FAB (fast atom bombardment) source, ESI (electro-spray ionization) source, MALDI (matrix assisted laser desorption and ionization) source. One of the most frequently used sources is the electronic impact EI source, wherein the substance of the sample either spontaneously evaporates or is already in the gas phase. A known energy electron flow hits the molecules of the sample, which are changed into positive ions by losing one or more electrons. The ions are then accelerated by an electrostatic field and directed towards the analyzer.

The diagram reporting the concentration of each ion versus the mass/charge (m/z) ratio, known as the mass spectrum, is distinctive of each compound as it is directly correlated to the chemical structure thereof as well as to the ionization conditions to which the compound is subjected. Typically, the mass spectrum is a series of peaks indicative of the relative abundances of detected ions as a function of their m/z ratios. The instruments employed in the mass spectrometry field, known as mass spectrometers, generally comprise three main units arranged in series: an ion source to volatize and ionize the sample, an analyzer to select the ions produced by the source according to the mass/charge ratio; and a detector to detect the ions coming from the analyzer. The mass spectrometer may also include electronics for processing output signals from the detector as needed to produce a user-interpretable mass spectrum.

The ion source is the part of the mass spectrometer entrusted to change the molecules of the sample into ions through the ionization phenomenon. Moreover the produced ions must be free to move in space for measurement of the m/z ratio. In certain "hyphenated" or "hybrid" systems, the sample supplied to the ion source may first be subjected to a form of analytical separation. For example, in a gas chromatography-mass spectrometry (GC-MS) system, the output of the GC column may be transferred into the ion source through appropriate GC-MS interface hardware.

The analyzer is the part of the mass spectrometer allowing for selecting the mass/charge (m/z) ratio of the ions produced by the source. Also this measurement can be carried out in many ways, so long as the ions can freely move in the spectrometer without colliding with air molecules, which is achieved by providing high-vacuum conditions therein.

According to the prior art, analyzers are mainly classified as magnetic analyzers, Omegatron analyzers (the mass selection is carried out by using a magnetic field and a RF field), quadrupole analyzers, ion-trap analyzers, FT-ICR (Fourier Transform Ion Cyclotron Resonance) analyzers, TOF (time of flight) analyzers, cycloidal mass analyzers (the mass selection is carried out through a suitable selection of the resulting electric and magnetic field), magnetic-sector and ion-trap analyzers, optic spectroscopy cross-wire analyzers (measurement of the spectra of either emission or absorption light, or of photons' effects on the analyzed sample). In the present work reference is made, by way of example, to the magnetic quadrupole, and ion-trap analyzers.

The magnetic analyzer comprises a bent tube immersed into a magnetic field perpendicular thereto. The magnetic field makes the ions cover a bent trajectory. The bend radius depends on the entering ions energy and on the magnetic field B. The ion exits the analyzer only if the ion trajectory corresponds to the tube bend. If the ion bends more or less than the tube bends, it collides with the tube walls and is neutralized. Therefore, for each value of the magnetic field only ions having a certain m/z ratio and a certain kinetic energy pass through the analyzer, while the others are removed. From the value of the magnetic field and from the kinetic energy it is possible to go back to the m/z ratio of the ion selected by the analyzer. In this way the mass spectrum, which is the graph of the intensity of the ionic current detected by the detector, is obtained depending on the m/z ratio selected by the analyzer. In a mass spectrum, the presence of a peak at a certain value of m/z indicates that the source is producing ions having that m/z ratio.

Another kind of analyzer frequently employed in the mass spectrometry is the quadrupole analyzer. Generally, a quadrupole is a device composed of four metal parallel bars. Each pair of diagonally opposed bars is electrically linked together and a RF (radio-frequency) voltage is applied between one pair of bars and the other pair. A direct current voltage is then added to RF voltage. Ions oscillate during the flight among the quadrupole bars. Only the ions having a certain m/z ratio pass through the quadrupole and reach the detector for a given ratio of the two voltages: the other ions undergo unstable oscillation and collide with the bars. This allows either the selection of a particular ion, or the scanning of the range of the masses by means of the voltage variation.

A further example of a mass analyzer consists of an ion-trap. Based on a physical principle similar to the one of the quadrupole, the ion-trap keeps all the ions within the trap and makes them selectively free upon varying of the intensity of an oscillating electric field.

The detectors generally comprise dynodes, i.e. electronic multipliers able to amplify the very feeble current produced by the ions passed through the analyzer. The signals obtained in this way are subsequently transmitted to a computer able to represent, with the aid of suitable software, the amount of each ion depending on its mass, i.e. the final mass spectrum. Moreover, the use of computers allows the instrument parameters to be quickly combined with the literature search in libraries of electronically formatted spectra, so as to automate the identification of compounds according to their spectra and to the operative conditions with which the analysis has been carried out.

With reference to FIG. 1, a mass spectrometer device of the kind based on an electronic impact source and on a quadrupole mass analyzer according to the known art is schematically shown. In FIG. 1, the device is denoted as a whole with the reference numeral 11 and it comprises an entrance section 11a, an ionization section 11b, an analysis section 11c and a detection section 11d.

The entrance section 11a is generally intended for being immersed in the ambient to be sampled, which generally reaches the atmospheric pressure, from which the gas to be sampled, or analyte, enters the device. To this purpose the entrance section 11a substantially comprises a capillary tube 13 with which a heater 15 is associated. The heater, for instance, has an electric resistance wound around the capillary tube 13. As it is known, to avoid effects due to absorption/desorption along the walls of the introduction system of gas, it is advisable to make a suitable choice of the materials as well as operating at a reasonably high temperature, for instance 100° C., which further allows for avoiding gas condensation phenomena.

In accordance with a prior art embodiment, the capillary tube 13 leads to a first transition chamber 17 defined inside a corresponding flange 19, and is discharged by means of a high-vacuum pump 21. The pump 21 for instance can be a turbo-molecular pump, associated through a duct 23 at a radial side door 25 and presenting the entrance axial primary door 43 associated with the casing 41 of the device.

Downstream of the first transition chamber 17 a second micro-capillary tube 27, for instance having an about 20 μm diameter and being about 1-2 mm long, is provided. The micro-capillary tube 27 communicates, in turn, with a second transition chamber 29, associated with the ionization section 11b, wherein the gas to be sampled is collected downstream the micro-capillary tube 27.

In the shown example, the ionization section 11b comprises an electronic impact (EI) source, wherein an ionization chamber 31 equipped with ionization device 33, for instance ionization filaments, is defined. Moreover, permanent magnets can be provided for increasing the source efficiency: in this way the electrons actually describe spiral trajectories so increasing the total path inside the source. Electrostatic lenses 35 are provided downstream the ionization chamber 31 in the transition area between the ionization chamber 33 and the following analysis section 11c. In the ionization chamber the molecules of the sample to be analyzed, which are in the gas phase, interact with an electron beam generated by an incandescent filament and accelerated through an adjustable potential. The beam energy is normally ranges between about 10 and 100 eV.

The analysis section 11c comprises a quadrupole device 37 downstream with the detection section 11d comprising a detector 39, for instance a Faraday cup detector and/or a SEM (secondary electron multiplier) detector or a Channeltron detector, is provided. The analysis section 11c and the detection section 11d are housed in the casing 41 at a pressure of generally on the order of at least $10^{-3}$ Pa, obtained through the turbo-molecular pump 21 associated through the corresponding axial primary door 43.

Calibrated leak devices are also known in the art. Devices of this kind allow generation of controlled gas flows through the membrane as well as to quantificate leakages value, by calibrating the instruments required to detect them, during tight tests. The currently used devices are substantially of two kinds: orifice leaks, or capillary, and helium permeation leaks. The first ones, also called pinholes, are generally made by laser ablation or chemical etching. Such technologies enable apertures to be manufactured with high precision and reproducibility. An example of the first kind of devices having membranes with nanoholes (holes passing through the membrane and having a nanometric size diameter) is disclosed in U.S. Pub. No. 2006/0144120. Devices of this kind allow for generating controlled gas flows through the membrane as well as to quantificate leakages values by calibrating the instruments required to detect them during tight tests. Another example of this kind of membrane is disclosed in WO 03/049840.

The permeation leaks however have a very unstable behavior when the temperature changes (their value varies of about 3% per centigrade grade in case of temperature values around room temperature), and long response times. They are fragile (being made of glass, they are easily breakable even when they only fall to the ground), only suitable for helium and have a single flow value. Examples of such permeation leaks are described in DE 19521275 and WO 02/03057.

Gas sampling devices based on permeation leaks are also disclosed in U.S. Pat. No. 4,008,388, U.S. Publication No. 2002/134933, U.S. Pat. No. 4,311,669, U.S. Pat. No. 4,712,008 and WO2008/074984. Selectively permeable membranes used in the field of mass spectrometry are also disclosed in U.S. Pat. No. 4,551,624 and Maden A M et al.: "Sheet materials for use as membranes in membrane introduction mass spectrometry," Anal. Chem., Am. Chem. Soc., US vol. 68, no. 10, 15 May 1996, pages 1805-1811, XP000588711 ISSN: 0003-2700.

Nanohole membranes of the above first species should not be confused with gas permeable membranes. Membranes of the first kind have holes made artificially, e.g. by focused ion beam (FIB) or laser drilling, having substantially regular cross section along the whole length of the hole, and for this reason can be calibrated according to the use of the membrane. In addition, several or many practically identical holes with parallel axes can be produced on the same membrane. On the contrary, gas permeable membranes are membranes whose natural property of the material allows for permeability of a gas or a gas mixture usually at a high temperature. In addition, gas permeable membranes may be selective in the type of gas allowed to permeate through the membrane, while nanohole membranes are not selective.

As it will be easily appreciated from the preceding description of a gas analyzer according to the known art, the entrance section and the ionization section are considerably complex both for the number of the components and for the fact that such components must be high-vacuum tight associated with each other, resulting in high costs. Moreover, the prior art devices must be equipped with vacuum pumps having considerable flow capacities as they have to absorb the flow entering the ionization chamber, which is generally high.

In addition to the foregoing considerations, to improve mass accuracy and resolution MS systems require calibration to correct for errors caused by various sources, such as drifts in instrument performance and response that may occur during an MS analysis and/or from one analysis to the next analysis. Calibration may entail introducing one or more calibrants into the mass spectrometer during an analysis or between analyses. A calibrant may be a known reference compound having a known response (e.g., peaks at specified m/z ratios) when processed by a given MS system. A calibration process may entail, for example, operating the MS system to make actual measurements of the calibrant ions, comparing the measurements to known measurements, and making adjustments to one or more components of the MS system as needed to tune the MS system. Conventionally, a relatively large amount of calibrant is injected into a mass spectrometer, which may have an adverse effect on the measurement of analyte ions derived from a sample of interest. Complex and costly vacuum pumping systems are often needed to successfully evacuate the calibrant from the mass spectrometer so as to minimize adverse impact on sample analysis. Moreover, again to minimize adverse impact on sample analysis, the use of a large amount of calibrant often results in a large period of "recovery" time being required to enable the mass spectrometer to be brought to standard operating conditions suitable for sample analysis. Additionally, the calibrant may clog up the small-bore capillaries often utilized to introduce gases into the ion sources of MS systems, such as electron ionization (EI) sources and chemical ionization (CI) sources.

Therefore, there continues to be a need for improved systems, devices and methods for calibrating MS systems.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for operating or calibrating a mass spectrometer (MS) includes: establishing a pressure differential across a membrane of the MS, wherein an upstream pressure in a calibrant gas inlet line on an upstream side of the membrane is greater than a downstream pressure in an ion source of the MS on a downstream side of the membrane; flowing a calibrant gas from the calibrant gas inlet line, through a nano-scale orifice of the membrane, and into the ion source; and while flowing the calibrant gas, maintaining the upstream pressure at a constant value.

According to another embodiment, a mass spectrometry (MS) system includes: a calibrant gas introduction system, a mass spectrometer, and a membrane interposed between the calibrant gas introduction system and the mass spectrometer, wherein the MS system is configured for performing any of the methods disclosed herein.

According to another embodiment, mass spectrometry (MS) system includes: a calibrant gas introduction system including a calibrant gas inlet line; a mass spectrometer including an ion source, an ion detector, and a membrane interposed between the calibrant gas inlet line and the ion source, the membrane including a nano-scale orifice communicating with the calibrant gas inlet line and the ion source; and a system controller communicating with the calibrant gas introduction system, and configured for maintaining an upstream pressure in the calibrant gas inlet line at a predetermined constant value.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 2:
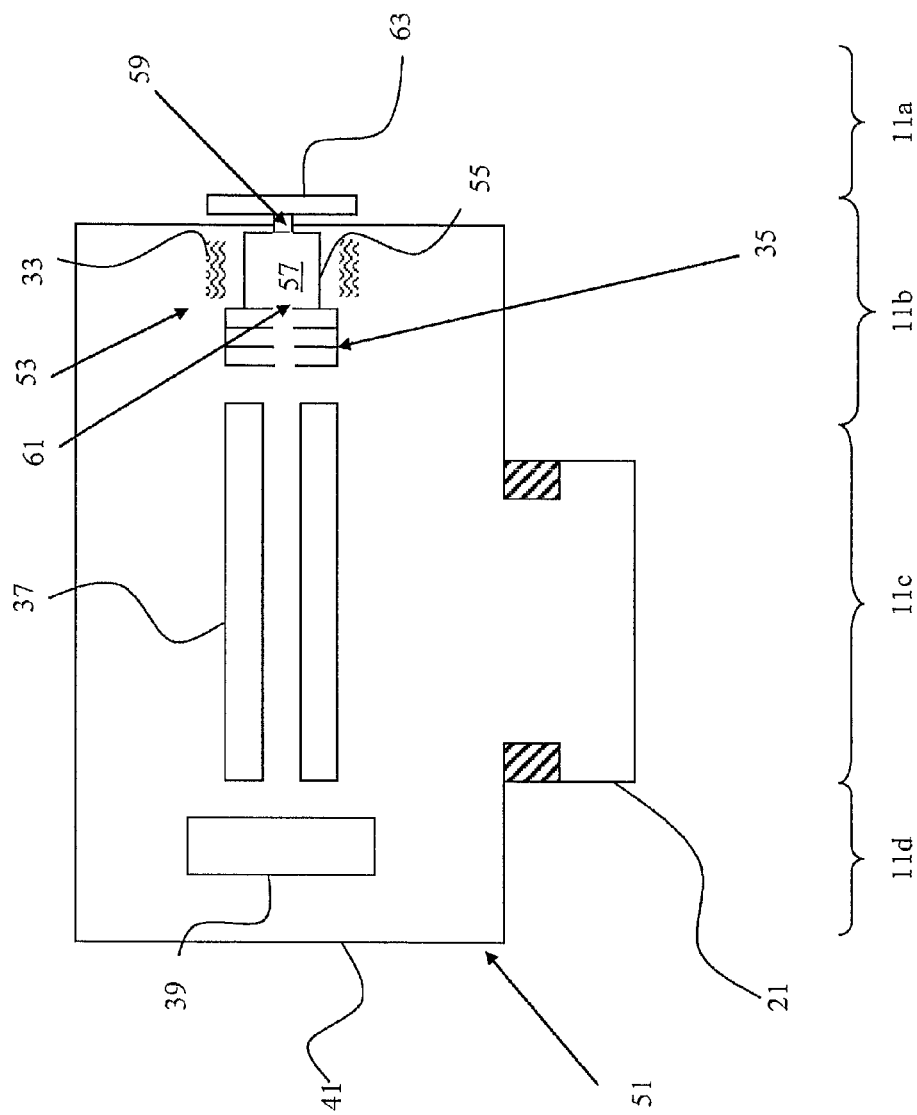
FIG. 2 is a schematic view of a gas analyzer incorporating an ionization device.

With reference to FIG. 2 a sampling device 53 is schematically shown. The device is incorporated into a gas analyzer 51. The sampling device 53 comprises a high-vacuum tight casing 55 inside which a high-vacuum tight ionization chamber 57 is defined. Chamber 57 is provided with a first inlet hole 59 (for example, 2-3 mm long) for the entrance of the gas to be sampled and is connected to the ambient downstream through a second outlet hole 61 for the gas exit.

According to the present invention, the first hole 59 is separated from the outside ambient by a high-vacuum tight membrane 63 having at least a nano-scale orifice (or nanohole), i.e. a hole having a diameter in the order of nanometers i.e. with diameters in a range between 10 nm and 500 nm (for example, about 20 nm-30 nm). The membrane 63 is substantially impermeable to the gas flow other than through the nanohole or nanoholes, and may include only one nanohole or a limited number of nanoholes (e.g., from ten to hundred nanoholes). The membrane 63, for instance with a square surface whose side length may be about 100 μm and whose thickness is for instance about 100 nm, is furthermore associated either with the walls of the ionization chamber 57 or with a duct associated therewith, through a high-vacuum tight coupling, for instance a suitable adhesive, a ring, a metal, or a VITON® gasket.

The high-vacuum tight membrane 63 is provided with at least one nanohole having a diameter in the order of nanometers, which develops through the membrane 63 along a substantially rectilinear axis. The nanohole may have a substantially uniform transverse cross-section.

The membrane may be substantially planar and the hole may develop through the membrane 63 along an axis, which is substantially perpendicular with respect to the surface of the membrane 63 and has a substantially uniform transverse cross-section. Moreover the nanohole may have a diameter D comprised between 10 nm and 500 nm.

The conductance C for a hole having a diameter in the order of nanometers (~100 nm), dividing two neighbouring spaces kept under differential vacuum conditions (of which one may be at atmospheric pressure (1,013 mbar) or lower and the other one under high-vacuum conditions (typically below $10^{-2}$ Pa, in the shown example), is measurable as:

$$C = \left(\frac{\frac{1}{4} \cdot (8 \cdot R \cdot T)}{\pi \cdot M}\right)^{1/2} \cdot A$$

where A is the hole surface, T is the gas temperature, R is the gas constant and M is the gas mass.

The concentration of the gas mixture when passing from the outside ambient to the ionization chamber 57 is therefore modified according to the above formula (gradually lighter gases will be present in higher concentrations inside the ionization chamber 57).

Inside the ionization chamber 57 the regime is however molecular and at the calibrated hole 61 for the exit of the ions towards the analyzer again a molecular flow regime will occur, which will be still adjusted by the same formula (gradually lighter gases exit in higher amounts). In all, by suitably defining the hole 61 size, it will be therefore possible restoring inside the ionization chamber 57 the same concentration distribution of the different gases forming the gas mixture in the ambient in which the sampling takes place (outside ambient at atmospheric pressure in the shown example).

Hole 61 will therefore have a diameter in the order of mm, preferably in the range between 1 and 10 mm, for instance 2.5 mm and a length in the order of mm, for instance 1 mm.

It is known that in an electron impact (EI) ion source, the bottom gas is ionized according to the equation:

$$I^+ = k_f I_e \cdot \sigma \cdot n \cdot l$$

where
$I_e$ is the emission current of the filament;
$\sigma$ is the ionization impact section;
n is the gas density;
l is the electrons path inside the source;
$k_f$ is the collection efficiency of the produced ions,
which can be also written as:

$$I^+ = I_e \cdot K(k_f, \sigma, l) \cdot P(\beta, n)$$

where K is the sensibility of the ion source that for a hydrogen Bayart-Alpert gauge is K=25 torr$^{-1}$ (19·10$^{-2}$ Pa$^{-1}$) and β is a constant depending on the kind of gas. Therefore, for a current $I_e$=4·10$^{-3}$ A at a pressure P=10$^{-7}$ mbar (10$^{-5}$ Pa) the corresponding ion current will be:

$$I^+ \approx 10^{-9} \text{ A}$$

If one would reach a sensibility in the order of 1 p.p.m. we will have:

$$I^+ \approx 10^{-15} \text{ A}$$

which corresponds to an order of magnitude for instance measurable by means of a Channeltron detector. Moreover, as the minimum current measurable by this kind of detector is on the order of $10^{-19}$ A, it will be theoretically possible to reach sensibilities in the order of p.p.b. fractions.

With a nanohole diameter in the membrane 63 of about 30 nm, at 1 bar ($10^{-5}$ Pa) a flow equal to:

$$\Phi = 2.3 \cdot 10^{-8} \text{ mbar} (2.3 \cdot 10^{-6} \text{ Pa})$$

will be obtained.

Assuming conductance of about 0.1 L/s through a hole 61 of about 2.0 mm diameter towards the quadrupole, inside the source a total pressure of about $10^{-7}$ mbar ($10^{-5}$ Pa) will occur, representing a value reachable for instance with a conventional ion pump.

The membrane 63 is able to be interposed between and separate two spaces kept under differential vacuum conditions and having pressures $p_u$ and $p_d$ respectively, where $p_u > p_d$, and wherein the membrane 63 has at least an orifice or nanohole able to determine a controlled gas flow depending on pressure $p_u$. The orifice may have a diameter D and a length L according to predetermined relation such as L<20·D.

The membrane 63 may be configured wherein the diameter D and the length L are such that the equivalent diameter $D_e$ of the orifice is $D_e$<100 nm, where $D_e$ is defined by the relationship $D_e = D \cdot a^{1/2}$, wherein a is the transmission probability of the orifice, depending on the L/D ratio, the orifice being able to operate under a molecular flow regime in a whole range of $P_u$ values, including the atmospheric pressure value. The aforementioned condition has in fact resulted to be particularly effective to avoid "clogging" phenomena due to contaminants introduced in the device because of its exposure in air, or originated by oils from backscattering of mechanical pumps used for vacuum generation or of other devices.

Preferably, the membrane 63 is made of ceramic, metallic, semiconductor material, or of a combination thereof, and the orifice is obtained by erosion with a highly focused ion beam (FIB).

Referring to FIG. 2, the sampling device 53 is incorporated into a gas analyzer 51 comprising an entrance section 11a, an ionization section 11b, an analysis section 11c and a detection section 11d. The entrance section 11a is intended for being immersed also in the atmosphere, i.e. for sampling gases at the atmospheric pressure, for the entrance of the gas to be sampled, or analyte, in the device and, according to the present invention, it incorporates the membrane 63. The ionization section 11b comprises an ionization chamber 57 for instance of the EI electronic impact kind and it is equipped with ionization device 33, for instance ionization filaments, or laser sources, radioactive sources, static plasma ionization sources, or radio-frequency sources. Electrostatic lenses 35 are provided downstream of the ionization chamber 57 in the transition area between the ion source and the following analysis section 11c. The analysis section 11c comprises a quadrupole device 37 and the detection section 11d comprises a detector 39, for instance a Faraday cup detector and/or a SEM (or a Channeltron) detector. At least a high-vacuum pump 21, for instance an ion pump, is provided in association with the casing 41 of the device 51 to discharge the internal ambient inside which the analysis section 11c and the detection section 11d are housed.

Figure 1:
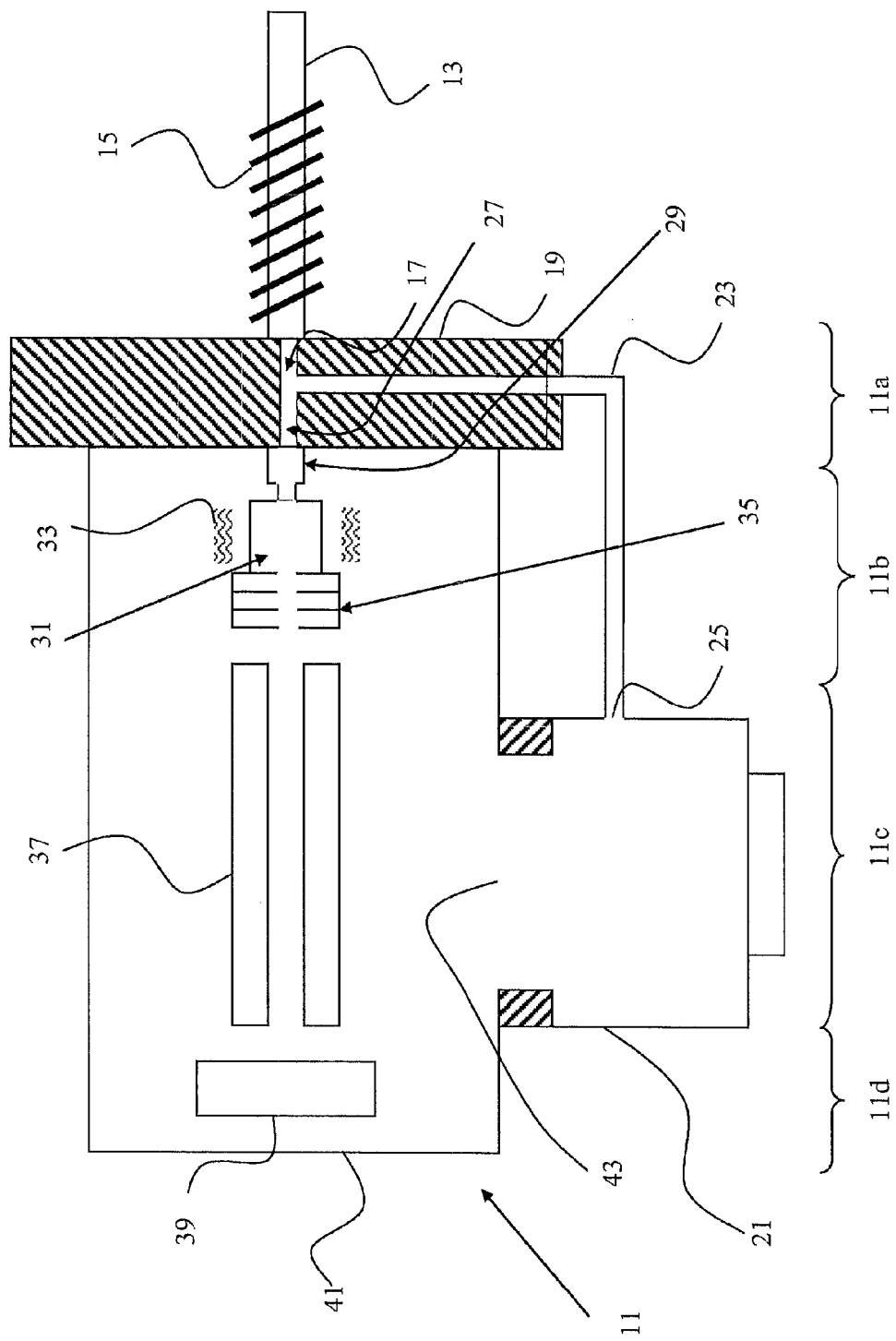
FIG. 1 is a schematic view of a gas analyzer according to the prior art.

Advantageously, as it becomes evident from a comparison with the prior art configuration shown in FIG. 1, the entrance section 11a is substantially reduced to only the membrane 63 with a resulting considerable simplification of the device and savings in the implementation cost. Such advantage becomes further evident from the fact that the high-vacuum pump can be replaced with a simple ion pump, due to the limited molecular flow passing through the membrane 63.

The molecular flow Φ which passes through the membrane 63 and, consequently, reaches the gas analyzer 51 is linked to the conductance C through the relationship:

$$\Phi = C \cdot (P_u - P_d)$$

where $p_u$ and $p_d$ are the pressures outside and inside the chamber 57 respectively.

The contained sizes of the nanohole (for instance in the order of 20-30 nm) and of the volume of the sampling chamber 57 (for instance in the order of $cm^3$ or of $cm^3$ fractions) are a considerable advantage since they involve substantially reduced response times associated with the sampling device and they considerably reduce the deterioration problems of the device in case of use in the presence of corrosive gases. Moreover, due to the provision of the nanoholes membrane, it is possible to implement sampling devices that are considerably simplified and consequently capable of being implemented as portable configurations.

Figure 3:
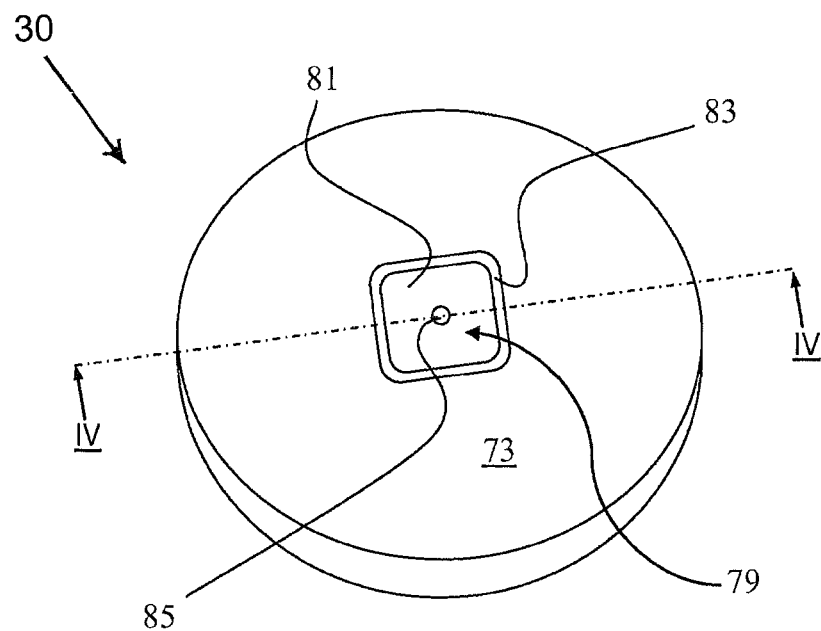
FIG. 3 is a perspective view of a support for an interface membrane that may be utilized at the inlet of a gas analyzer or mass spectrometer.
Figure 4:
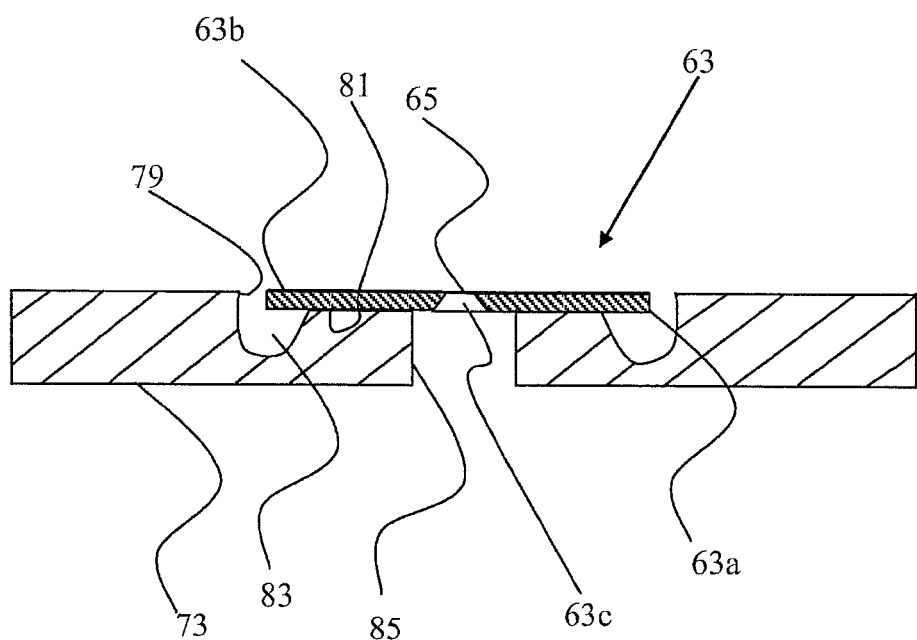
FIG. 4 is a cross-sectional view taken along line IV-IV of FIG. 3 when incorporating the membrane.

With reference to FIGS. 3 and 4, the membrane 63 may include a substrate (or first layer) 63a and a surface cover layer (or second layer) 63b. In some embodiments, the membrane 63 is composed of silicon (Si) and the surface cover layer 63b is composed of silicon nitride (SiN). The layer 63b made of silicon nitride may face the space having higher pressure $p_u$, while the substrate 63a faces the space having lower pressure $p_d$. In an exemplary embodiment of the membrane 63, the substrate 63a has a thickness ranging from about 0.1 mm to 0.3 mm, and the layer 63b has a thickness of 200 nm.

According to the present invention, the membrane 63, in particular the face of the layer 63b, which is turned towards the space having higher pressure, can further be subjected, depending on the requirements, to surface coating such as applying a waterproof coating, in order to avoid water vapor generation, which could contribute to cause the event known as "clogging", the obstruction of the nanohole or nanoholes and consequently the interruption or reduction of the molecular flow of analyte from the section having higher pressure to the section at lower pressure.

In other embodiments, the membrane 63 can advantageously be associated to heating means, which may also be provided to avoid clogging risks. The membrane 63 is preferably accommodated in a membrane support 73 advantageously provided with an appropriate well 79 in which the membrane 63 can be housed or mounted. Furthermore the support 73 may be made of metal, e.g. copper. The support 73 may have, for example, a disc-like shape having a diameter ranging from about 20 mm to 25 mm and a thickness ranging from about 1.5 mm to 2.5 mm.

In the illustrated example, the well 79 is substantially defined at the center of the support 73 and is a square, seen according to a plan view, into which a membrane 63 having a complementary shape can be accommodated. In this exemplary embodiment, the membrane 63 may be for example a square, seen according to a plan view, having a side length ranging from about 3.0 mm to 8.0 mm and a thickness of about 0.20 mm, and the well 79 may have a side length ranging from about 5.0 mm to 10.0 mm.

Moreover the well 79 further comprises a bearing zone (or resting zone) 81 for the membrane 63, preferably located in the center and positioned at a slightly lowered height with respect to the surface of the support 73, so that when the membrane 63 rests on the zone 81, the perimeter edges of the well 79 prevent the lateral escape of the membrane, thereby facilitating the mounting. In other words, it is sufficient that the perimeter sides of the well 79 determine a resting perimeter for the membrane 63 when this rests on the central zone 81.

The central zone 81 of the support 73 is further surrounded by a channel 83, in which an adhesive substance, e.g. a sealing resin, can be distributed in order to hold the membrane 63 on the support 73. The resting perimeter defined by the perimeter edges of the well 79 may be spaced from the sides of the membrane 63 in order to allow the adhesive to flow out from the channel 83 when the membrane 63 is located on the resting zone 81 and to facilitate in this manner a perfect adhesion of the membrane 63 to the support 73. Advantageously, the channel 83 can be obtained by means of mechanical machining or by means of electrical discharge machining or laser ablation, which may be carried out so as to make the inner surface rough in such a manner to guarantee the optimal adhesion of the adhesive material distributed thereon. The resting zone 81 of the support 83 further comprises an aperture 85 located at the nanohole 65 provided in the membrane 63. If the membrane 63 has more than one nanohole, the aperture 85 may be provided with a size, and/or a number of apertures may be provided, adequate to avoid obstructing the nanoholes.

In the exemplary embodiment shown, the nanohole 65 is advantageously made at a thinner central zone 63c of the membrane 63, wherein the substrate 63a has been removed and there is only the layer 63b. The thinner zone is, for example, substantially a square with a side length ranging from 20 μm to 500 μm. Other embodiments are however possible wherein the nanohole or nanoholes 65 are made in the membrane 63, without removing the substrate 63a or by removing it only partially. Accordingly the nanohole or nanoholes in the membrane 63 are made only in the layer 63b or in both the layer 63b and the substrate 63a. Moreover, the support 73, the well 79 and the membrane 63 may assume substantially any shape, e.g. circular, square, rectangular, rhombus-like, irregular, etc., according to the needs.

Although the subject matter has been disclosed with particular reference to an ion source of the EI type, it is however possible to provide the employment of the sampling device in combination with other kinds of ion sources.

Moreover, although the subject matter has been disclosed with reference to an analyzer of the quadrupole kind, it is however possible to employ the sampling device in combination with other kinds of analyzers, such as for instance magnetic analyzers, Omegatron analyzers, ion-trap analyzers, FT-ICR (Fourier Transform ion cyclotron resonance) analyzers, TOF (time of flight) analyzers, cycloidal mass analyzers, magnetic-sector and ion-trap analyzers, or optic spectroscopy cross-wire analyzers.

According to a further aspect, the sampling device may be used in a predetermined gas leaks detector and it will therefore be equipped with a specific mass spectrometer, considerably simplified with respect to the quadrupole, and suitably tuned to detect the gas of interest. For instance, the sampling device may be used in a helium leaks device wherein, as known, a current signal proportional to the concentration of helium ions in the ambient to be sampled is generated. Similarly, it will also be possible to take advantage of the device in the field of leaks detection in devices using smelling probes.

According to the present disclosure, a calibrant gas may be introduced into a mass spectrometer under constant-pressure, very low flow conditions. The calibrant gas may be introduced between analyte sample runs (e.g., externally) or during analyte sample runs (e.g., internally). In either case, the calibrant gas is introduced under conditions that do not adversely impact the sample analysis. Examples of embodiments relating to the introduction of calibrant gas will now be described with reference to FIGS. 5-8B.

Figure 5:
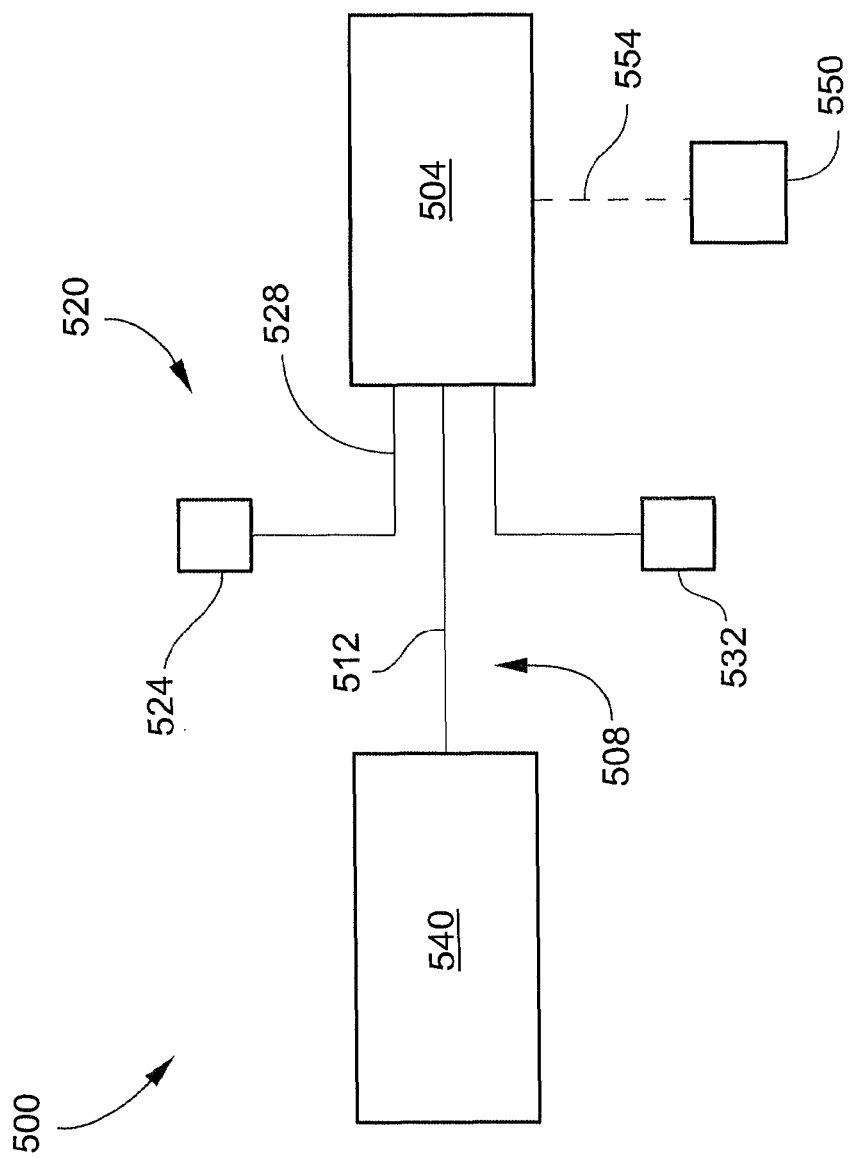
FIG. 5 is a schematic view of an example of a mass spectrometry (MS) system according to one embodiment.

FIG. 5 is a schematic view of an example of a mass spectrometry (MS) system 500 according to one embodiment of the present teachings. The MS system 500 generally includes a mass spectrometer 504 interfaced with a sample source via a sample interface 508. The structure and operation of various types of mass spectrometers and associated components are generally understood by persons skilled in the art, and thus will be described only briefly. The sample interface 508 may include a sample transfer line 512 through which the analyte-containing sample is conducted into the mass spectrometer 504, and may be configured to isolate the low-pressure or vacuum regions in the mass spectrometer 504 from the higher-pressure regions outside the mass spectrometer 504. The mass spectrometer 504 may include a housing in which an ion source, a mass analyzer, and an ion detector are located. The mass spectrometer 504 may also include a vacuum system (i.e., one or more vacuum pumps and associated plumbing) for controlling the pressure in one or more regions within the housing.

The ion source may be any device suitable for producing analyte ions from a sample stream received from the sample interface 508 and directing the as-produced ions into the mass analyzer. For example, the ion source may be an electron ionization (EI) apparatus, a chemical ionization (CI) apparatus, a photo-ionization (PI) apparatus, or a field ionization (FI) apparatus. The ion source may also include the capability of switching between EI and CI modes of operation. As appreciated by persons skilled in the art, the ion source may include an ionization chamber and an ionization device. In the case of EI or CI, the ionization device is typically a filament configured for emitting electrons for interaction with the sample in a manner understood by persons skilled in the art.

The mass analyzer may be any device configured for separating, sorting or filtering analyte ions on the basis of their respective m/z ratios. Examples of mass analyzers include, but are not limited to, multipole electrode structures (e.g., mass filters, ion traps), time-of-flight (TOF) components, ion cyclotron resonance (ICR) traps, electrostatic analyzers (ESAs), and magnetic sectors. The mass analyzer may include a system of more than one mass analyzer, particularly when ion fragmentation is desired. As examples, the mass analyzer may be a tandem MS or MS$^n$ system, as appreciated by persons skilled in the art. As another example, the mass analyzer may include a mass filter followed by a collision cell, which in turn is followed by a mass filter or other mass analyzing device.

The ion detector may be any device configured for collecting and measuring the flux (or current) of mass-discriminated ions outputted from the mass analyzer. Examples of ion detectors include, but are not limited to, electron multipliers, photomultipliers, and Faraday cups.

The MS system 500 also includes a calibration system 520. The calibration system 520 may include one or more calibrant sources 524, one or more calibrant gas inlet lines 528, and associated components (e.g., conduits, valves, restrictors, mass flow controllers, pressure regulators, pumps, heaters, etc.) for controlling the flow of calibrants into the ion source. In the illustrated example, the calibrant source 524 includes a calibrant source containing a calibrant utilized for calibrating one or more components of the mass spectrometer 504 such as the ion source. This type of calibrant may be referred to herein as an "instrument calibrant" or an "ion source calibrant." The MS system 500 may also include one or more other sources 532 (depicted collectively in the schematic view) for other types of calibrants such as, for example, external calibrants for producing calibration curves before or after analyzing a sample, and internal calibrants (e.g., internal references masses, or IRMs) that are introduced into the ion source together with the analyte sample. While FIG. 5 depicts separate inlet lines for different calibrant gases, this is merely a schematic depiction. A single inlet line may serve more than one calibrant source. Depending on its type, a calibrant may be supplied initially as a gas or as a liquid, the latter of which may be flowed into the mass spectrometer 504 utilizing a suitable carrier gas. The other source(s) 532 may also be schematically representative of other types of gases that may be introduced into the mass spectrometer 504, such as CI reagent gases (when operating in CI mode) such as methane, or cleaning gases such as nitrogen, argon, etc.

The illustrated MS system 500 may also be representative of a hyphenated system in which an analytical separation apparatus such as, for example, a gas chromatograph (GC) 540, serves as the sample source for the mass spectrometer 504. Accordingly, the MS system 500 may in some embodiments be considered as being a GC-MS system. In such an embodiment, the MS system 500 may be interfaced with the GC 540 via the sample interface (or GC-MS interface) 508. The structure and operation of various types of GCs and associated components are generally understood by persons skilled in the art, and thus will be described only briefly. The GC 540 may generally include a housing, a carrier gas source, a sample introduction device typically mounted at the housing and communicating with a sample source, a GC column disposed in the housing, and a heating device configured for indirect heating (e.g., a GC oven) or direct heating (e.g., resistive heating element) of the GC column. In this case, the analyte-containing sample is conducted from the GC column into the mass spectrometer 504 via the sample transfer line 512, which in some embodiments may be an extension of the GC column. The sample interface 508 may be configured to isolate the low-pressure or vacuum regions of the mass spectrometer 504 from the higher-pressure regions (e.g., atmospheric pressure) of the GC 540. The sample may be a matrix that includes sample material to be analytically separated in the GC column and one or more solvents, and which is carried by a carrier gas (e.g., helium, nitrogen, argon, hydrogen, etc.) through the GC column and into the ion source.

The MS system 500 may also include a system controller 550. The system controller 550 may be configured for controlling and/or monitoring various aspects of the MS system 500, such as sample introduction into the ion source, operation ion source's filament or other ionization device, introduction of ion source calibrants and other calibrants, introduction of other gases such as reagent gas (if applicable) and cleaning gas, vacuum settings, pressure settings, gas flow rate settings, temperature settings or implementation of varying temperature programs, operating parameters of the mass analyzer (e.g., applied electric and/or magnetic fields, collision/background gas introduction, timing of ion optics, and the like), acquisition and analysis of signals from the ion detector, generation and display of mass spectra or chromatograms, and so on. For these purposes, the system controller 550 is schematically illustrated as being in signal communication with the mass spectrometer 504 via a communication link 554. The communication link 554 may be representative of several communication links respectively interfacing with various components of the MS system 500. Other communication links to other components of the MS system 500 are, for simplicity, not specifically shown. A given communication link may be wired or wireless. Also for these purposes, the system controller 550 may include one or more types of hardware, firmware and/or software, as well as one or more types of memory. As appreciated by persons skilled in the art, the system controller 550 may, for example, include an electronic processor, a database stored in memory, and software for implementing various functions for controlling the components. The system controller 550 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the system controller 550 (e.g., logic instructions embodied in software, data, and the like). The system controller 550 may include an operating system (e.g., Microsoft Windows® software) for controlling and managing various functions of the system controller 550. One or more components of the system controller 550 may be located remotely from the MS system 500 and communicate with the local portion of the system controller 550 over a wired or wireless communication link. In some embodiments, the system controller 550 may include or be part of a laboratory information management system (LIMS), e.g., as may be utilized in a hospital or other medical setting.

Figure 6:
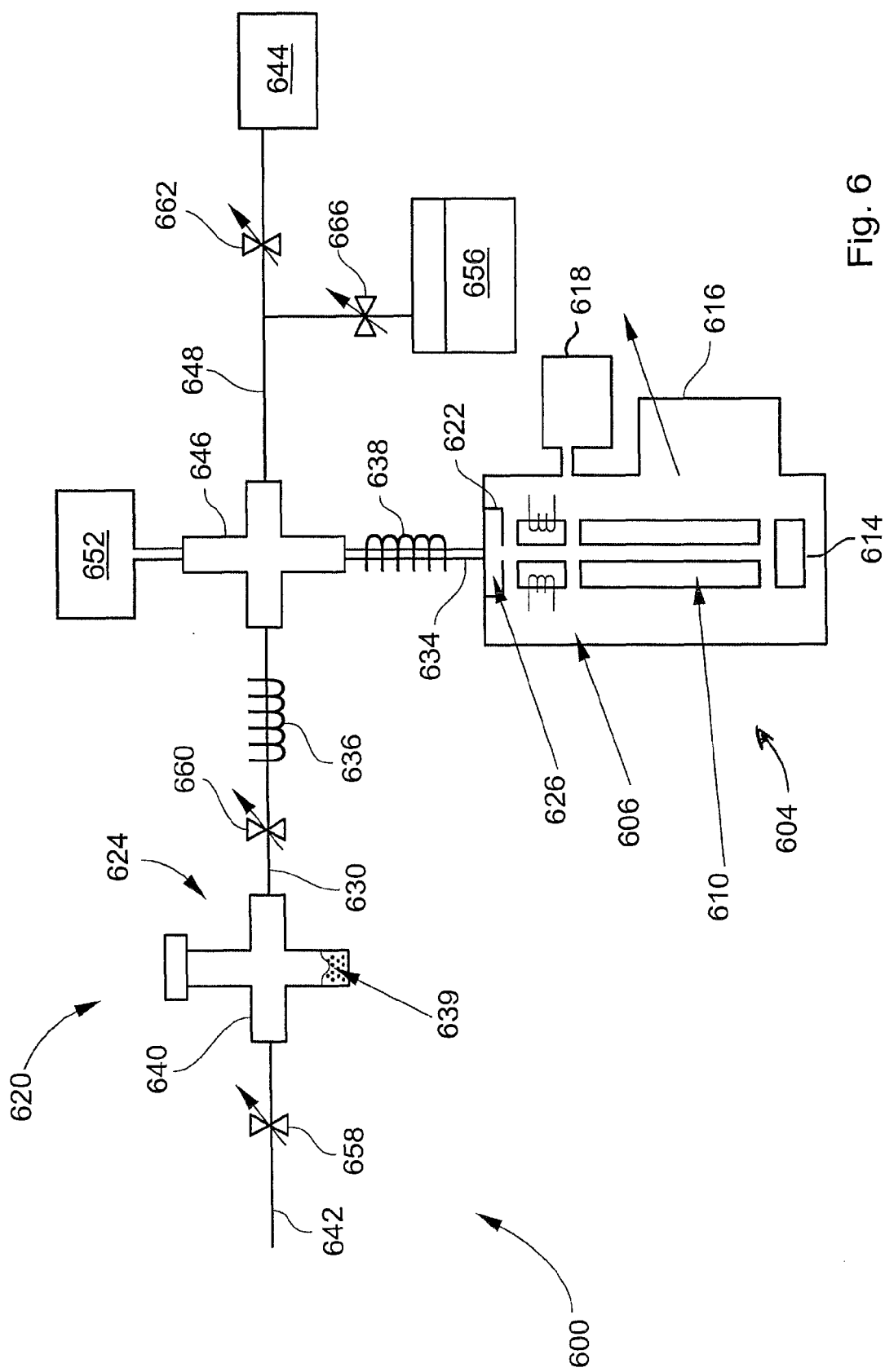
FIG. 6 is a schematic view of an example of an MS system according to another embodiment.

FIG. 6 is a schematic view of an example of an MS system 600 according to another embodiment. The MS system 600 may generally include a mass spectrometer 604 interfaced with a calibrant gas introduction system 620. The mass spectrometer 604 is shown by example as including an EI or CI ion source 606, a mass analyzer 610 in the form of a single quadrupole device (by example only), an ion detector 614, a vacuum pump 616 suitable for maintaining a very low internal pressure (on the scale of, for example, about $10^{-8}$ to $10^{-2}$ mbar) in the mass spectrometer 604, and an ion gauge 618 for monitoring the internal pressure. The MS system 600 also includes a gas inlet or interface 622 that provides a fluidly isolated interface between the calibrant gas introduction system 620 and the ion source 606. The gas inlet 622 includes one or more membranes 626 (or "nano-membranes"), each of which includes one or more nano-scale orifices (or "nano-holes") through its thickness, as described by example herein.

The calibrant gas introduction system 620 generally includes a calibrant gas source 624 communicating with a calibrant gas line 630, 634. As illustrated, the calibrant gas line 630, 634 may include one or more distinct sections, including a section (line 634) that leads directly to at least one nanohole of at least one membrane 626 of the gas inlet 622. The coupling or interface between the calibrant gas line 634 and the membrane 626 may be done in any fluidly sealed manner. One or more heating devices 636 and 638 may be provided along the calibrant gas line(s) 630 and 634 as needed for maintaining the calibrant gas at a desired temperature. In the example specifically shown in FIG. 6, the calibrant gas source 624 includes a reservoir 639 for an initially liquid-phase calibrant such as, for example, perfluorotributylamine (or FC-43, or PFTBA), which is commonly utilized for calibrating EI ion sources. As this type of calibrant is initially provided as a liquid, the calibrant gas source 624 provides or communicates with a tee-connection or manifold 640 with an upstream carrier gas line 642 leading from a source (not shown) of a suitable carrier gas such as, for example, krypton, whereby the calibrant is entrained in the carrier gas and the mixture flows through the downstream calibrant gas line 630, 634. In other embodiments, the calibrant is initially provided in a gas phase and a carrier gas is not needed. Alternatively, the calibrant may be an internal reference mass compound such as, for example, perfluoroethyltriazine (PFET, or $C_9F_{15}N_3$), or may be an external calibrant such as may be utilized to generate calibration curves.

The calibrant gas introduction system 620 may also include a pressure controller for controlling the pressure of the calibrant gas in the calibrant gas line 634, i.e., on the upstream side (or input side) of the membrane 626. The pressure controller may include, for example, a suitable pump 644 and other hardware such as valves, restrictors, or the like. In the illustrated example, the pump 644 is located downstream of the calibrant gas source 624, and another tee-connection or manifold 646 is provided between two sections of the calibrant gas line 630 and 634 and a gas outlet line 648 that leads to the pump 644. Hence, in this example the second tee-connection 646 provides a junction between the calibrant gas source 624 and the pump 644, and with the gas inlet 622 containing the membrane 626. A suitable pressure transducer 652 (e.g., an absolute capacitive gauge) may be tapped into this tee-connection 646, or alternatively may be positioned in operative communication with the calibrant gas line 630 and 634 at any other location thereof as needed for monitoring the pressure of the calibrant gas on the upstream side of the membrane 626. Also shown by way of example is a cleaning gas source 656 that utilizes the calibrant gas introduction system 620 to supply cleaning gas to the mass spectrometer 604.

The flow of gases through the calibrant gas introduction system 620 may be controlled by any suitable means. In the illustrated embodiment, a first valve 658 controls the flow of carrier gas from the carrier gas source, a second valve 660 controls the flow of calibrant gas (or, in this example, the mixture of calibrant gas and carrier gas) from the calibrant gas source 624. A third valve 662, between the second valve 660 and the pump 644, controls whether the calibrant gas is flowed into the ion source 606 or vented from the calibrant gas introduction system 620 to the pump 644. A fourth valve 666 controls the flow of cleaning gas from the cleaning gas source 656. The valves 658, 660, 662, 666 may be manually or automatically controlled. For instance, one or more of the valves 658, 660, 662, 666 may communicate with a system controller (see, e.g., FIG. 5) and controlled by control signals. In addition to open/closed (ON/OFF) positions, one or more of the valves 658, 660, 662, 666 may be variable between open and closed positions. For example the third valve 662, or both the second valve 660 and the third valve 662, may be variable valves that control the pressure of the calibrant gas on the inlet side of the membrane 626. In one embodiment, the system controller maintains a desired or predetermined calibrant gas pressure on the upstream side of the membrane 626 (or upstream pressure) by controlling the pump 644 and/or controlling the third valve 662 (or both the second valve 660 and the third valve 662), based on feedback received from the pressure transducer 652. The upstream pressure setting may be inputted to the system controller by a user or by software. The system controller may be configured to make adjustments to the pump 644 and/or one or more valves 660 and 662 as needed to maintain the upstream pressure at the desired, constant value, or to change the upstream pressure to a new, constant value requested by the user or software.

Although not specifically shown in FIG. 6, it will be understood that the MS system 600 may include an interface suitable for placing a sample gas transfer line from a sample source (e.g., the GC shown in FIG. 5) in communication with the ion source 606. In some embodiments, the sample gas transfer line is separate from the calibrant gas inlet line 634 and may be a conventional line that extends directly into the ion source 606, such as from a GC column. In other embodiments, the sample gas may flow through a membrane featuring a nano-scale orifice. For example, the sample gas line may be coupled to a separate membrane in communication with a nano-scale orifice of the separate membrane. In another example, the membrane 626 shown in FIG. 6 may include a plurality of nano-scale orifices. In this example, the calibrant gas inlet line 634 may communicate with one nano-scale orifice (or one group of nano-scale orifices), and the sample transfer line may communicate with a different nano-scale orifice (or a different group of nano-scale orifices) of the same membrane 626. In another example, the sample transfer line and the calibrant gas inlet line 634 may be coaxial, such that one of the gases flows through an inner conduit and the other gas flows through the annular space formed by an outer conduit coaxially surrounding the inner conduit. In this latter example, the sample transfer line and the calibrant gas inlet line 634 may communicate with the same nano-scale orifice (or group of nano-scale orifices) or with different nano-scale orifices. In another example, the sample transfer line may be coupled with the calibrant gas inlet line 634 upstream of the membrane 626.

It will also be understood that in some embodiments, the MS system 600 illustrated in FIG. 6 may be interfaced with a GC, such as described above in conjunction with FIG. 5, or with another type of analytical separation instrument. It will also be understood that MS system 600 illustrated in FIG. 6 may be configured for introducing other types of gases in the mass spectrometer 604, such as CI reagent gases.

When installed at the gas inlet 622, the membrane 626 is effective for fluidly isolating (i.e., in a vacuum-tight manner) the calibrant gas introduction system 620 from the interior of the mass spectrometer 604, such that the only flow path for the calibrant gas is through the nano-scale orifice(s) of the membrane 626, and such that a large or small pressure differential across the membrane 626 may be maintained as desired. The calibrant gas flows through the nano-scale orifice under the influence of a pressure differential defined by a higher upstream pressure on the upstream side of the membrane 626 (i.e., in the calibrant gas line 634) and a lower downstream pressure on the downstream side of the membrane 626 (i.e., in the ion source 606). In relation to the interior of the mass spectrometer 604, the upstream pressure and downstream pressure may also be referred to as the "outside" or "external" pressure and "inside" or "internal" pressure, respectively. In some embodiments, this pressure differential (i.e., the difference between the upstream pressure and downstream pressure) may range from 1 to 11 orders of magnitude. For example, the mass spectrometer 604 may be operated with the downstream pressure ranging from $10^{-8}$ mbar to $10^{-2}$ mbar, and the calibrant gas may be conducted to the membrane 626 under a constant upstream pressure ranging from 0.1 mbar to 1000 mbar (or 1 bar, or 1 atm). In other embodiments, the constant upstream pressure may range from 10-500 mbar, 10-200 mbar, 10-100 mbar, 20-70 mbar, or 20-50 mbar. Under an appropriate pressure differential, and with the membrane's orifice having a nanometric size, the calibrant gas may be introduced into the mass spectrometer 604 via the membrane 626 at a very low flow rate, which herein is also termed a "nanoflow" flow rate. In some embodiments, the flow rate of the calibrant gas ranges from $10^{-7}$ sccm to $10^{-5}$ sccm (standard cubic centimeters per minute), which range is an example of a nanoflow flow rate. This greatly reduced flow rate is in large contrast to the conventional flow rates implemented for calibrant gas in MS systems, the lowest of which is typically 1-2 sccm. In some embodiments, the flow of the calibrant gas through the nano-orifice may be characterized as occurring in or near a molecular gas flow regime.

FIGS. 3 and 4, described above, illustrate one example of a gas inlet interface 30 that may be utilized at the gas inlet 622 of the mass spectrometer 604. The gas inlet interface 30 may include the membrane 63, or both the membrane 63 and the membrane support 73. One or more nano-scale orifices 65 may be formed through the thickness of the substrate 63a. The substrate 63a may be composed of any suitable material, such as a ceramic, metal or semiconductor. The substrate 63a may have any suitable shape such as, for example, rectilinear (as illustrated), polygonal, circular, or elliptical. The support 73 may be composed of any suitable material. The support 73 may have any suitable shape such as, for example, rectilinear, polygonal, circular or disk-shaped (as illustrated), or elliptical. The support 73 may include a well 79 in which the membrane 63 is disposed (i.e., mounted). In the illustrated example, the well 79 is rectilinear but may have any other suitable shape. The shape of the well 79 may be complementary to that of the membrane 63. The support 73 may include an aperture 85 aligned with the nano-scale orifice 65 to provide a flow path for gas through the support 73 from the nano-scale orifice 65. In embodiments providing a plurality of nano-scale orifices, the aperture 85 may be sized large enough to communicate with more than one nano-scale orifice, or an aperture may be provided in alignment with each corresponding nano-scale orifice. A central zone 65c of thinner membrane material may be formed in the substrate 63a, and the nano-scale orifice 65 may be formed in the layer 63b (which may be a thinner layer as described above) so as to open at the central zone 63c. The central zone 63c may have a circular, polygonal or irregular shape. In some embodiments, the nano-scale orifice 65 may be considered as being a single hole formed through the entire thickness of the substrate 63c. The nano-scale orifice 65 may be formed by any technique suitable for the thickness and composition of the substrate 63c, a few non-limiting examples being laser drilling, mechanical drilling, focused ion beam (FIB) etching or other suitable dry etching, or wet etching.

Generally, the nano-scale orifice 65 may have an inside diameter D ranging from about 1 nm to 1000 nm. In some embodiments, the nano-scale orifice 65 may have an inside diameter D ranging from 10 nm to 500 nm. In some embodiments, the nano-scale orifice 65 may have a length L as defined above in relation to the inside diameter D. In some embodiments, the nano-scale orifice 65 may have an equivalent diameter $D_e$ as defined above in relation to the transmission probability and L/D ratio.

Additional examples of membranes that may be suitable in the context of the present disclosure are described in U.S. Patent Application Publication Nos. 2011/0006201 and 2011/0006202, the entire contents of which are incorporated by reference herein.

An example of a method for operating a mass spectrometer will now be described. For illustrative purposes, reference is primarily made to the mass spectrometer 604 and associated MS system 600 shown in FIG. 6. Also in this example, FC-43 is employed as the instrument calibrant with the understanding that other instrument calibrants, external calibrants, or internal calibrants may alternatively be employed. Liquid-phase FC-43 may be loaded in the reservoir 639. The mass spectrometer 604 may be prepared as needed for operation (e.g., purging, cleaning, start-up of heaters 630 and 634, etc.), and evacuated down to a downstream pressure suitable for operating the ion source 606 and mass analyzer 610. The downstream pressure may be set in the range noted earlier in this disclosure. The vacuum pump(s) 616 responsible for evacuation may be controlled by a system controller such as the system controller 550 described above and illustrated in FIG. 5. The membrane 626 ensures a pressure differential in which the upstream pressure in the calibrant gas introduction system 620 is higher than the downstream pressure in the mass spectrometer 604. The nano-orifice(s) in the membrane 626 are very small and thus do not affect the pressure differential. Flow of the FC-43 in gas phase is then established by opening the valves 658, 660 and 662 and operating the pump 644, which may be controlled by the system controller 550 as described above. The calibrant gas (e.g., the mixture of FC-43 and krypton or other carrier gas) flows through the calibrant gas inlet line 630, 634, through the nano-orifice(s) of the membrane 626, and into the ion source 606. The pressure differential across the membrane 626 is maintained at a desired level by maintaining the upstream pressure at a constant value. In the present example, this may be accomplished by operating the system controller 550 to monitor readings from the pressure transducer 652, compare the as-measured pressure to a desired set point pressure, and making adjustments as needed to maintain the constant upstream pressure. Adjustments may include adjusting the pump 644 and/or one or more of the valves 658, 660 and 662. In the present context, the term "constant value" or "constant upstream pressure" is intended to encompass not only a single value, but also a single value within a range of tolerance (e.g., 30 mbar+/−1 mbar). The upstream pressure (and thus the pressure differential) may be set to ensure that the calibrant gas flows at a very low flow rate, such as within the range noted earlier in this disclosure.

The ion source 606 ionizes the calibrant gas and any ionizable components of background gas that may be present in the ion source 606. The resulting ions are transferred into the mass analyzer 610 and scanned out to the ion detector 614. Signals indicative of the ion current measured by the detector 614 are transmitted to the system controller 550 for processing, which may include generating a mass spectrum or other representation of the ions detected. The data acquired in this manner may be utilized to calibrate the ion source 606 and/or other components of the mass spectrometer 604. For instance, the calibrant ion signal measurement may be compared to known reference values for the particular calibrant ion to determine whether the ion source 606 and/or other components of the mass spectrometer 604 need to be adjusted. Such instrument adjustments may include, for example, mass axis or peak position adjustments, adjustments that improve mass resolution, and adjustments to MS operating parameters such as gas flow rates, voltages applied to the ion source 606 or electrodes or ion optics of the mass spectrometer 604, etc.

After performing the instrument calibration, the MS system 600 may be operated to analyze a sample in a known manner. The analyte sample may be introduced into the mass spectrometer 604 from a suitable source such as, for example, the GC 540 illustrated in FIG. 5. As noted earlier in this disclosure, other calibrations such as mass-axis calibration may be performed as needed, utilizing external and/or internal calibrants.

In some embodiments, the calibrant may be introduced into the mass spectrometer 604 at the same time as the analyte sample. The analyte sample may be introduced into the ion source in a conventional manner and at a conventional flow rate. In some embodiments, the analyte sample flow rate may be 2-8 orders of magnitude higher than the calibrant flow rate, or the calibrant flow rate may be 2-8 orders of magnitude lower than the analyte sample flow rate. The calibrant may have little or no effect measurement of the sample, in view of the low flow rate at which the calibrant is injected into the ion source 606 and the small amount of calibrant utilized.

Figure 7A:
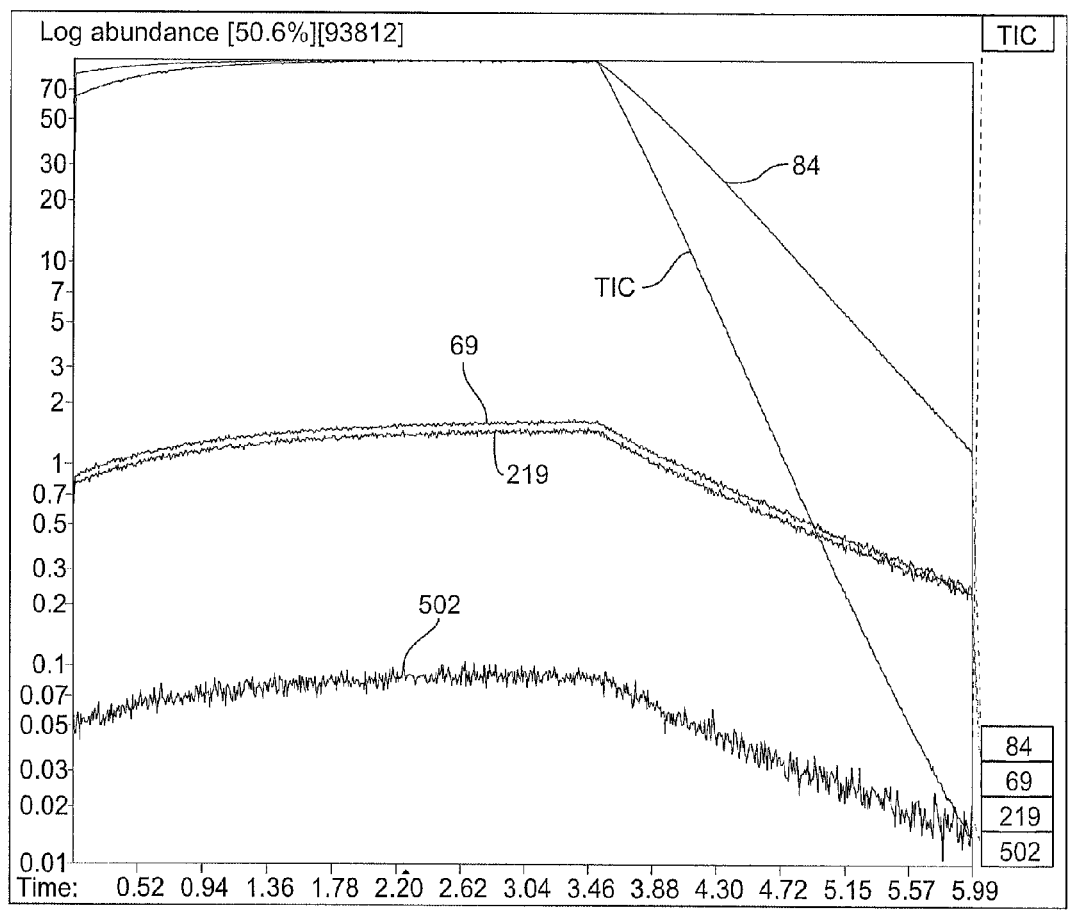
FIG. 7A is a chromatogram (log abundance vs. time in minutes) resulting from running a mixture of FC-43 and krypton through an MS system similar to that shown in FIG. 6.
Figure 7B:
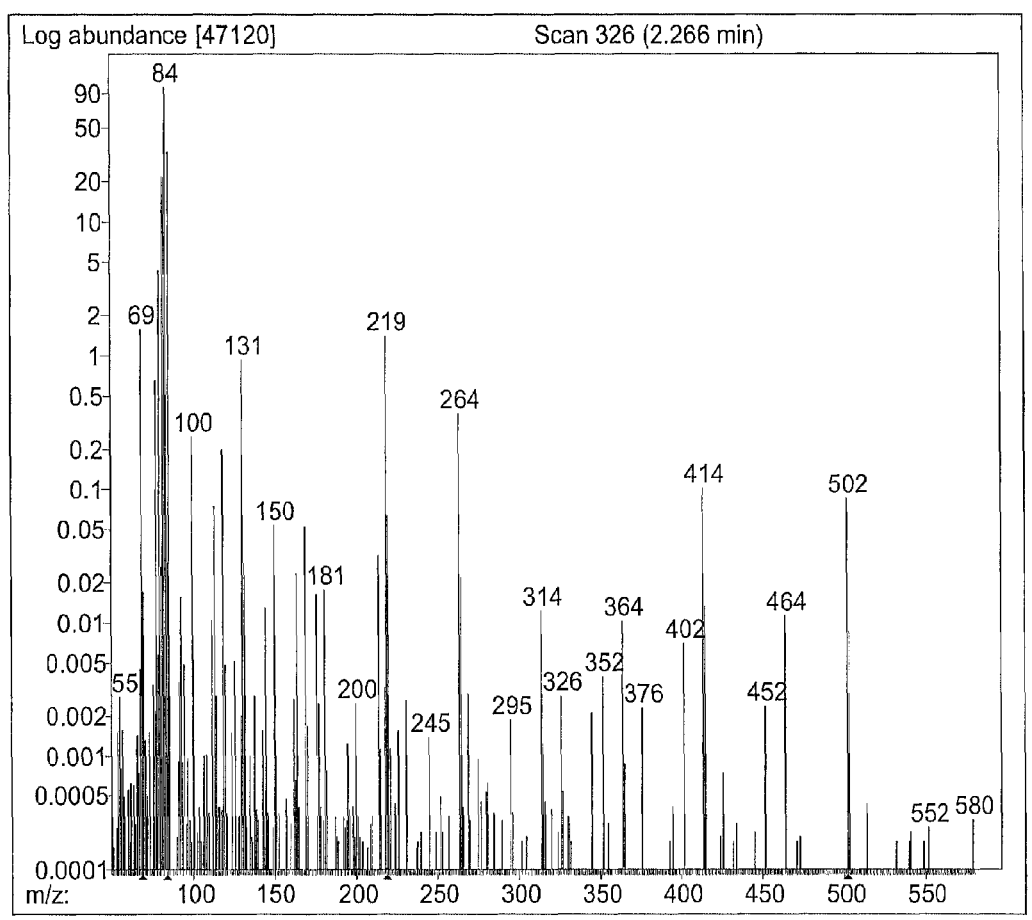
FIG. 7B is a mass spectrum (log abundance vs. m/z ratio) resulting from the same test associated with FIG. 7A.
Figure 8A:
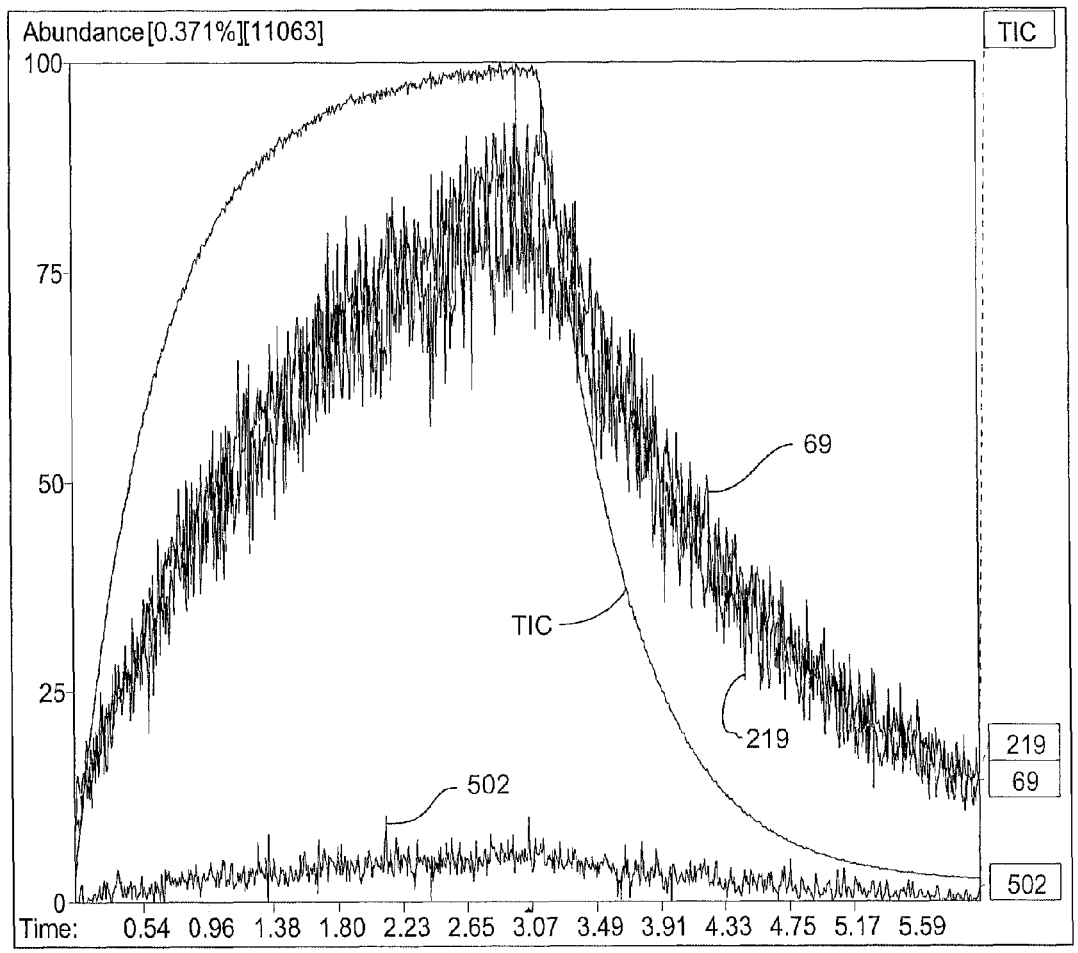
FIG. 8A is a chromatogram resulting from running the mixture through the same MS system and under the same conditions as the test associated with FIGS. 7A and 7B, except at a different upstream pressure.
Figure 8B:
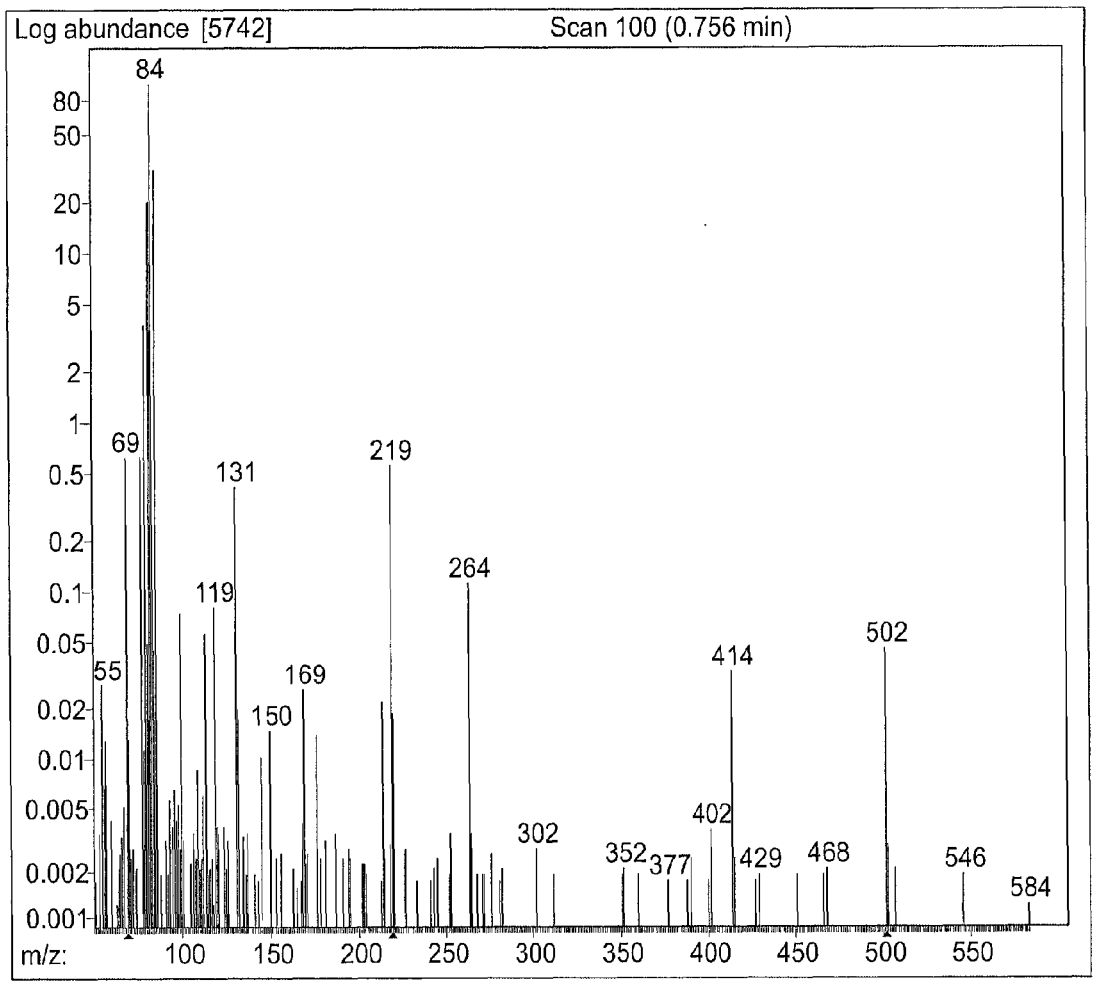
FIG. 8B is a mass spectrum resulting from the same test corresponding to FIG. 8A.

FIG. 7A is a chromatogram (log abundance vs. time in minutes) resulting from running a mixture of FC-43 and krypton through an MS system similar to that shown in FIG. 6, and measuring ion current for six minutes. The upstream pressure was fixed at 500 mbar (almost 375 Torr) while the downstream pressure was $2\text{-}3\times10^{-7}$ Torr. The flow rate of the mixture was $10^{-7}$ to $10^{-5}$ sccm. The traces correspond to masses 69, 219 and 502 associated with FC-43, mass 84 associated with krypton, and the total ion current (TIC). Injection of the mixture was shut off at 3.46 minutes, as reflected in the decreasing signals after this point in time. FIG. 7B is a mass spectrum (log abundance vs. m/z ratio) resulting from the same test. Strong mass peaks of the calibrant above the background noise are evident. FIG. 8A is a chromatogram resulting from running the mixture through the same MS system and under the same conditions as the test associated with FIGS. 7A and 7B, except that the upstream pressure was fixed at 60 mbar (almost ten times less than that of the test associated with FIGS. 7A and 7B). FIG. 8B is a mass spectrum resulting from the same test corresponding to FIG. 8A.

FIGS. 7A to 8B demonstrate that a calibrant may be introduced into an MS system at a constant pressure and very low flow rate, and produce data readily usable for calibration purposes even though quite a small amount of calibrant is utilized. It is expected that the small amount of calibrant utilized may have a negligible impact on the measurement of target analytes of a sample run through the MS system. Consequently, it is expected that the calibrant may alternatively be run through the MS system at the same time as an analyte sample with little or no adverse impact. FIGS. 7A to 8B also demonstrate that the calibrant ion signals may be modulated simply by varying the upstream pressure. Thus, for example, the upstream pressure may be increased in the event a stronger calibrant ion signal is desired.

One or more advantages may be obtained from implementation of the systems, devices and methods described herein. The flow of calibrant gas into the mass spectrometer via the membrane as described above is controllable merely by maintaining the upstream pressure at a constant value, and may be done at a very low flow rate. In other words, injection of the calibrant into the mass spectrometer is performed and controlled at a constant pressure, rather than at a constant flow as is conventionally done. This may eliminate the need for conventional hardware such as flow meters. Mass spectral data of the instrument calibrant of a quality effective for calibration purposes may be obtained utilizing a reduced and optimized amount of calibrant gas. Reducing the amount of calibrant utilized may reduce or eliminate any adverse impact the calibrant may have on the sensitivity or other performance criterion of the mass spectrometer when operated normally to measure the target analytes of an actual sample. The reduced amount of calibrant may also have negligible impact on the associated vacuum system and the setting of the vacuum level in the mass spectrometer. The vacuum hardware and other mechanical hardware may thus be simplified, thereby reducing the cost of the MS system. For example, smaller and simpler turbomolecular pumps may be utilized. After instrument calibration, the recovery time of the MS system, i.e., the time required for the MS system to return to standard operating conditions for sample analysis, may be significantly reduced.

Exemplary Embodiments

Exemplary embodiments provided in accordance with the presently disclosed subject matter include, but are not limited to, the following:

1. A method for operating a mass spectrometer (MS), the method comprising: establishing a pressure differential across a membrane of the MS, wherein an upstream pressure in a calibrant gas inlet line on an upstream side of the membrane is greater than a downstream pressure in an ion source of the MS on a downstream side of the membrane; flowing a calibrant gas from the calibrant gas inlet line, through a nano-scale orifice of the membrane, and into the ion source; and while flowing the calibrant gas, maintaining the upstream pressure at a constant value.

2. The method of embodiment 1, comprising maintaining the downstream pressure in the ion source in a range from $10^{-8}$ mbar to $10^{-2}$ mbar.

3. The method of embodiment 1 or 2, wherein the constant value of the upstream pressure ranges from 0.1 mbar to 1000 mbar.

4. The method of any of embodiments 1-3, wherein flowing the calibrant gas flows through the nano-scale orifice is done at a flow rate ranging from $10^{-7}$ sccm to $10^{-5}$ sccm.

5. The method of any of embodiments 1-4, comprising operating the ion source to produce calibrant ions and operating a detector of the MS to generate a calibrant ion signal.

6. The method of embodiment 5, comprising adjusting an intensity of the calibrant ion signal by adjusting the upstream pressure to a new value, and maintaining the upstream pressure at the new value.

7. The method of embodiment 6, comprising adjusting one or more operating parameters of the MS based on the generated calibrant ion signal.

8. The method of embodiment 5, comprising, after generating the calibrant ion signal, flowing a sample gas into the ion source.

9. The method of embodiment 8, comprising, before flowing the sample gas, ceasing flow of the calibrant gas.

10. The method of embodiment 8 or 9, comprising flowing the sample gas into the ion source from a sample gas inlet line separate from the calibrant gas inlet line.

11. The method of any of embodiments 8-10, comprising producing sample ions in the ion source and generating a mass spectrum of the sample ions.

12. The method of any of embodiments 8-11, comprising flowing an additional gas into the ion source, wherein the additional gas is selected from the group consisting of a chemical ionization reagent, an internal reference mass, and both a chemical ionization reagent and an internal reference mass.

13. The method of any of embodiments 8-12, comprising flowing the sample gas from a gas chromatograph.

14. The method of any of embodiments 1-7, comprising, while flowing the calibrant gas, flowing a sample gas into the ion source.

15. The method of embodiment 14, comprising flowing the sample gas at a flow rate ranging from 2 to 8 orders of magnitude higher than the calibrant gas flow rate.

16. The method of any of embodiments 1-15, comprising flowing the calibrant gas through the nano-scale orifice together with a carrier gas.

17. A mass spectrometry (MS) system, comprising: a calibrant gas introduction system, a mass spectrometer, and a membrane interposed between the calibrant gas introduction system and the mass spectrometer, wherein the MS system is configured for performing any of the methods disclosed herein.

18. The MS system of embodiment 17, comprising a gas chromatograph communicating with a sample inlet of the mass spectrometer.

19. A mass spectrometry (MS) system, comprising: a calibrant gas introduction system comprising a calibrant gas inlet line; a mass spectrometer comprising an ion source, an ion detector, and a membrane interposed between the calibrant gas inlet line and the ion source, the membrane including a nano-scale orifice communicating with the calibrant gas inlet line and the ion source; and a system controller communicating with the calibrant gas introduction system, and configured for maintaining an upstream pressure in the calibrant gas inlet line at a predetermined constant value.

20. The MS system of embodiment 19, wherein the calibrant gas introduction system comprises a pressure transducer configured for measuring the upstream pressure and a pressure controller configured for controlling the upstream pressure, wherein the system controller is configured for receiving measurements of the upstream pressure from the pressure transducer and controlling the pressure controller based on the measurements.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 550 schematically depicted in FIG. 5. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 550 in FIG. 5), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable

What is claimed is:

1. A method for calibrating a mass spectrometer (MS), the method comprising:
   establishing a pressure differential across a membrane of the MS wherein an upstream pressure in a calibrant gas inlet line on an upstream side of the membrane is greater than a downstream pressure in an ion source of the MS on a downstream side of the membrane;
   flowing a calibrant gas from the calibrant gas inlet line, through a nano-scale orifice of the membrane, and into the ion source at a nanoflow flow rate, wherein said nano-scale orifice is formed through said membrane along a substantially rectilinear axis; and
   while flowing the calibrant gas, maintaining the upstream pressure at a constant value.

2. The method of claim 1, comprising maintaining the downstream pressure in the ion source in a range from $10^{-8}$ mbar to $10^{-2}$ mbar.

3. The method of claim 1, wherein the constant value of the upstream pressure ranges from 0.1 mbar to 1000 mbar.

4. The method of claim 1, wherein flowing the calibrant gas flows through the nano-scale orifice is done at a flow rate ranging from $10^{-7}$ sccm to $10^{-5}$ sccm.

5. The method of claim 1, comprising operating the ion source to produce calibrant ions and operating a detector of the MS to generate a calibrant ion signal.

6. The method of claim 5, comprising adjusting an intensity of the calibrant ion signal by adjusting the upstream pressure to a new value, and maintaining the upstream pressure at the new value.

7. The method of claim 5, comprising adjusting one or more operating parameters of the ion source based on the generated calibrant ion signal.

8. The method of claim 5, comprising, after generating the calibrant ion signal, flowing a sample gas into the ion source.

9. The method of claim 8, comprising, before flowing the sample gas, ceasing flow of the calibrant gas.

10. The method of claim 8, comprising flowing the sample gas into the ion source from a sample gas inlet line separate from the calibrant gas inlet line.

11. The method of claim 8, comprising producing sample ions in the ion source and generating a mass spectrum of the sample ions.

12. The method of claim 8, comprising flowing an additional gas into the ion source, wherein the additional gas is selected from the group consisting of a chemical ionization reagent, an internal reference mass, and both a chemical ionization reagent and an internal reference mass.

13. The method of claim 8, comprising flowing the sample gas from a gas chromatograph.

14. The method of claim 1, comprising, while flowing the calibrant gas, flowing a sample gas into the ion source.

15. The method of claim 14, comprising flowing the sample gas at a flow rate ranging from 2 to 8 orders of magnitude higher than the calibrant gas flow rate.

16. The method of claim 1, comprising flowing the calibrant gas through the nano-scale orifice together with a carrier gas.

17. A mass spectrometry (MS) system, comprising: a calibrant gas introduction system, a mass spectrometer, and a membrane interposed between the calibrant gas introduction system and the mass spectrometer, wherein the MS system is configured for performing the method of claim 1.

18. The MS system of claim 17, comprising a gas chromatograph communicating with a sample inlet of the mass spectrometer.

19. A mass spectrometry (MS) system, comprising:
   a calibrant gas introduction system comprising a calibrant gas inlet line;
   a mass spectrometer comprising an ion source, an ion detector, and a membrane interposed between the calibrant gas inlet line and the ion source, the membrane comprising a nano-scale orifice communicating with the calibrant gas inlet line and the ion source, wherein said nano-scale orifice is formed through said membrane along a substantially rectilinear axis; and
   a system controller communicating with the calibrant gas introduction system, and configured for maintaining an upstream pressure in the calibrant gas inlet line at a predetermined constant value.

20. The MS system of claim 19, wherein the calibrant gas introduction system comprises a pressure transducer configured for measuring the upstream pressure and a pressure controller configured for controlling the upstream pressure, wherein the system controller is configured for receiving measurements of the upstream pressure from the pressure transducer and controlling the pressure controller based on the measurements.

* * * * *